(12) United States Patent
Castor

(10) Patent No.: US 10,954,248 B2
(45) Date of Patent: Mar. 23, 2021

(54) BRYOID COMPOSITIONS, METHODS OF MAKING AND USE THEREOF

(71) Applicant: Aphios Corporation, Woburn, MA (US)

(72) Inventor: Trevor Percival Castor, Arlington, MA (US)

(73) Assignee: APHIOS CORPORATION

( * ) Notice: Subject to any disclaimer, the term of this patent is extended or adjusted under 35 U.S.C. 154(b) by 0 days.

(21) Appl. No.: 16/208,919

(22) Filed: Dec. 4, 2018

(65) Prior Publication Data

US 2019/0194222 A1    Jun. 27, 2019

Related U.S. Application Data

(63) Continuation of application No. 14/647,237, filed as application No. PCT/US2013/072070 on Nov. 26, 2013, now abandoned.

(60) Provisional application No. 61/730,227, filed on Nov. 27, 2012.

(51) Int. Cl.
| | | |
|---|---|---|
| *A61P 31/12* | (2006.01) | |
| *A61P 31/22* | (2006.01) | |
| *A61P 31/18* | (2006.01) | |
| *A61P 25/14* | (2006.01) | |
| *A61P 25/28* | (2006.01) | |
| *A61P 25/00* | (2006.01) | |
| *A61P 25/16* | (2006.01) | |
| *A61P 27/06* | (2006.01) | |
| *A61P 35/00* | (2006.01) | |
| *A61K 31/365* | (2006.01) | |
| *C07D 493/22* | (2006.01) | |

(52) U.S. Cl.
CPC .......... *C07D 493/22* (2013.01); *A61K 31/365* (2013.01)

(58) Field of Classification Search
CPC   A61P 31/12; A61P 31/22; A61P 31/18; A61P 25/14; A61P 25/28; A61P 25/00; A61P 25/16; A61P 27/06; A61P 35/00; A61K 31/365; C07D 493/22
See application file for complete search history.

(56) References Cited

PUBLICATIONS

Pettit et al., J. Am. Chem. Soc., 1982, 104, 6846-6848.*

* cited by examiner

*Primary Examiner* — Sun Jae Yoo

(57) ABSTRACT

Embodiments of the present invention feature novel Bryoid compositions, methods of making and methods of treating disease.

3 Claims, 24 Drawing Sheets

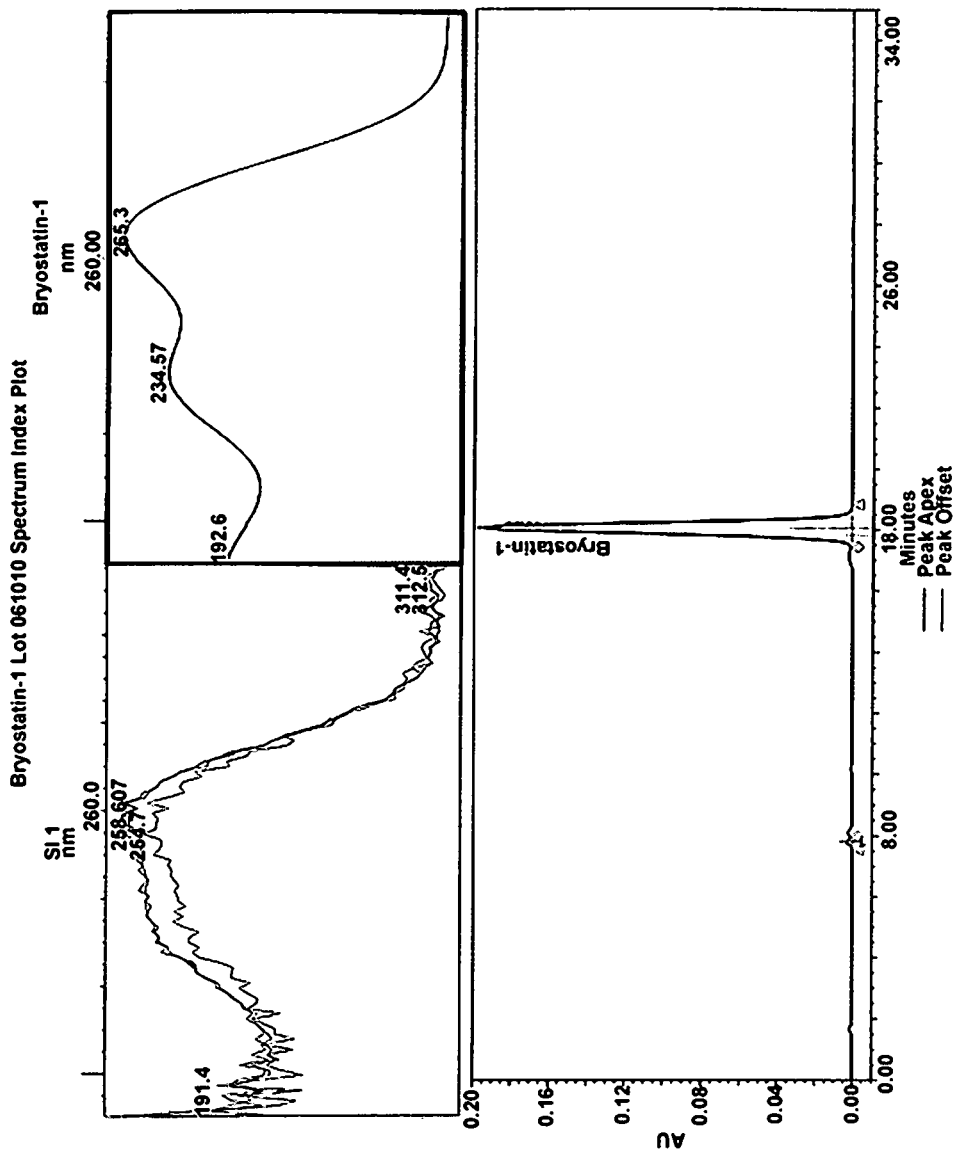
Figure 1: HPLC Chromatographic Scan of Bryostatin-1

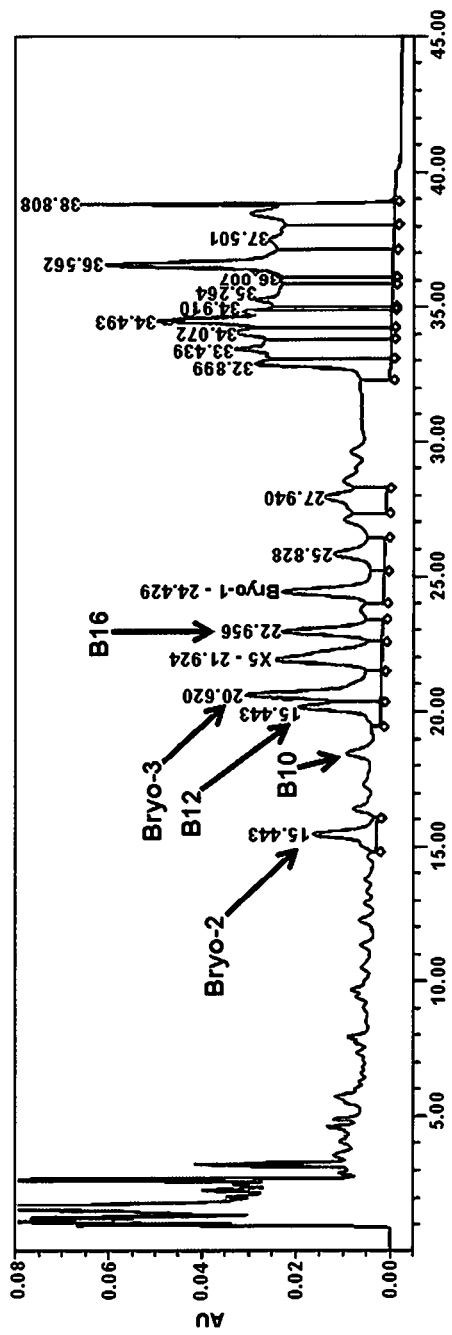
Figure 2: HPLC Chromatogram of *B. neritina* EA crude extract

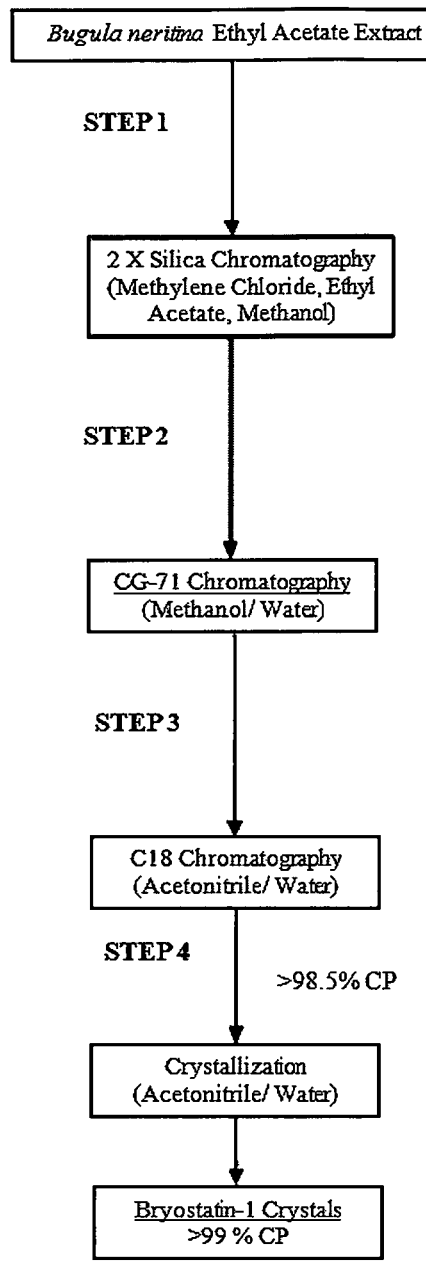
Figure 3: Flow Chart Detailing Steps Used to Purify Bryostatin-1

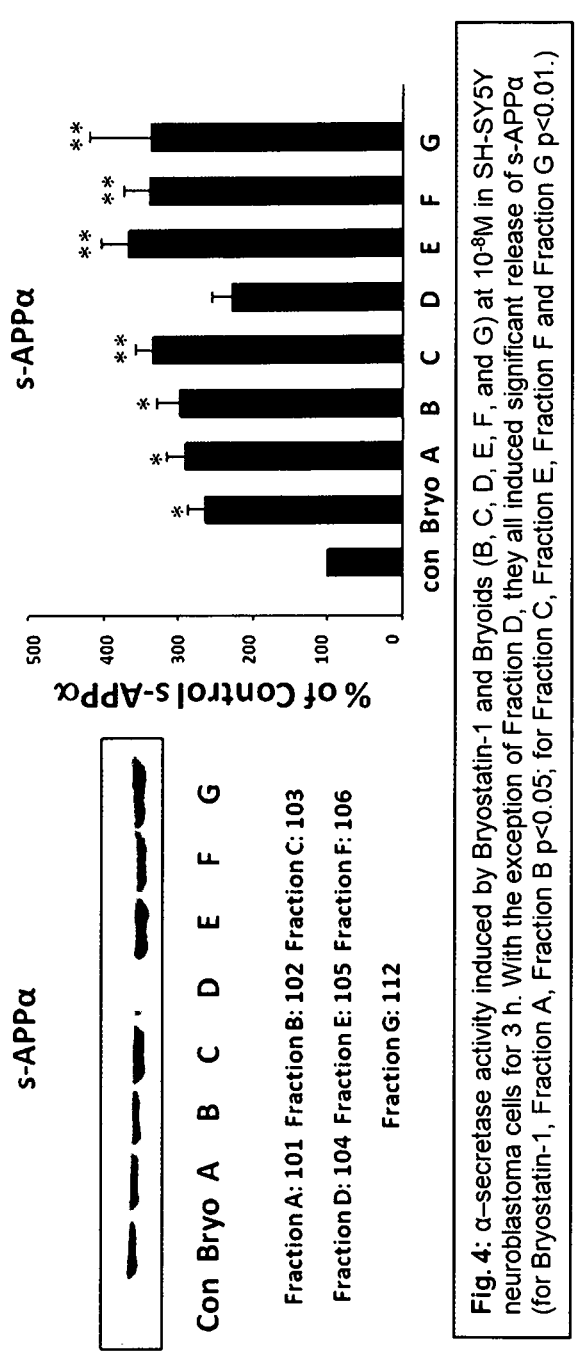
Fig. 4: α-secretase activity induced by Bryostatin-1 and Bryoids (B, C, D, E, F, and G) at $10^{-8}$M in SH-SY5Y neuroblastoma cells for 3 h. With the exception of Fraction D, they all induced significant release of s-APPα (for Bryostatin-1, Fraction A, Fraction B $p<0.05$; for Fraction C, Fraction E, Fraction F and Fraction G $p<0.01$.)

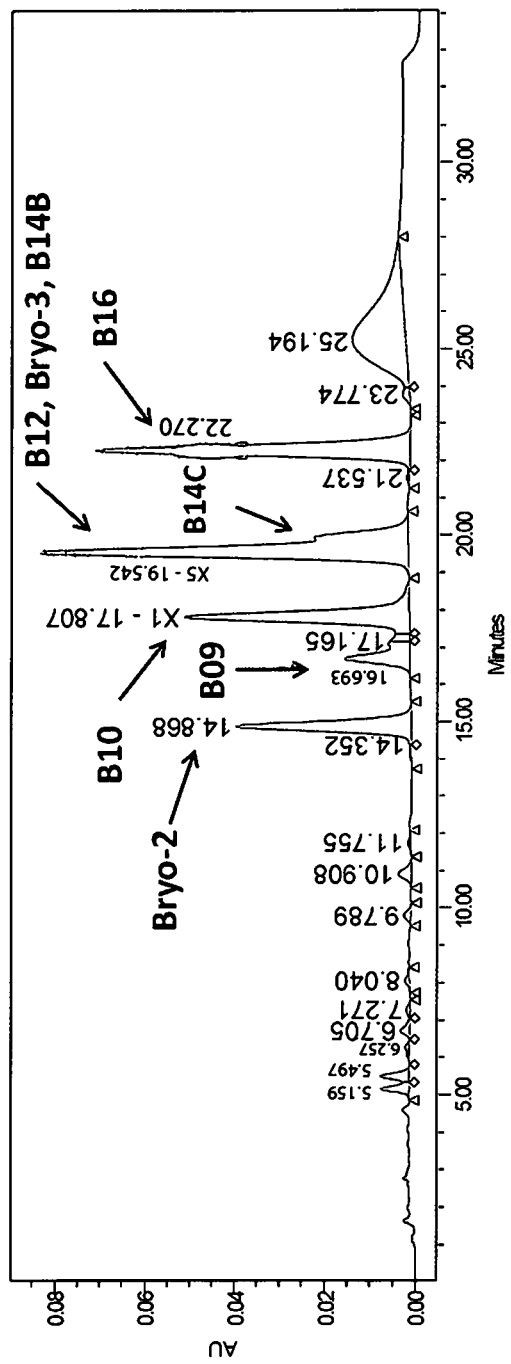
Figure 5: HPLC Chromatogram of Bryoids Mixture monitored at 265 nm. Bryostatin-1 was not included, and B12, B14B, and Bryo-3 co-elute. All have Bryostatin-like UV patterns.

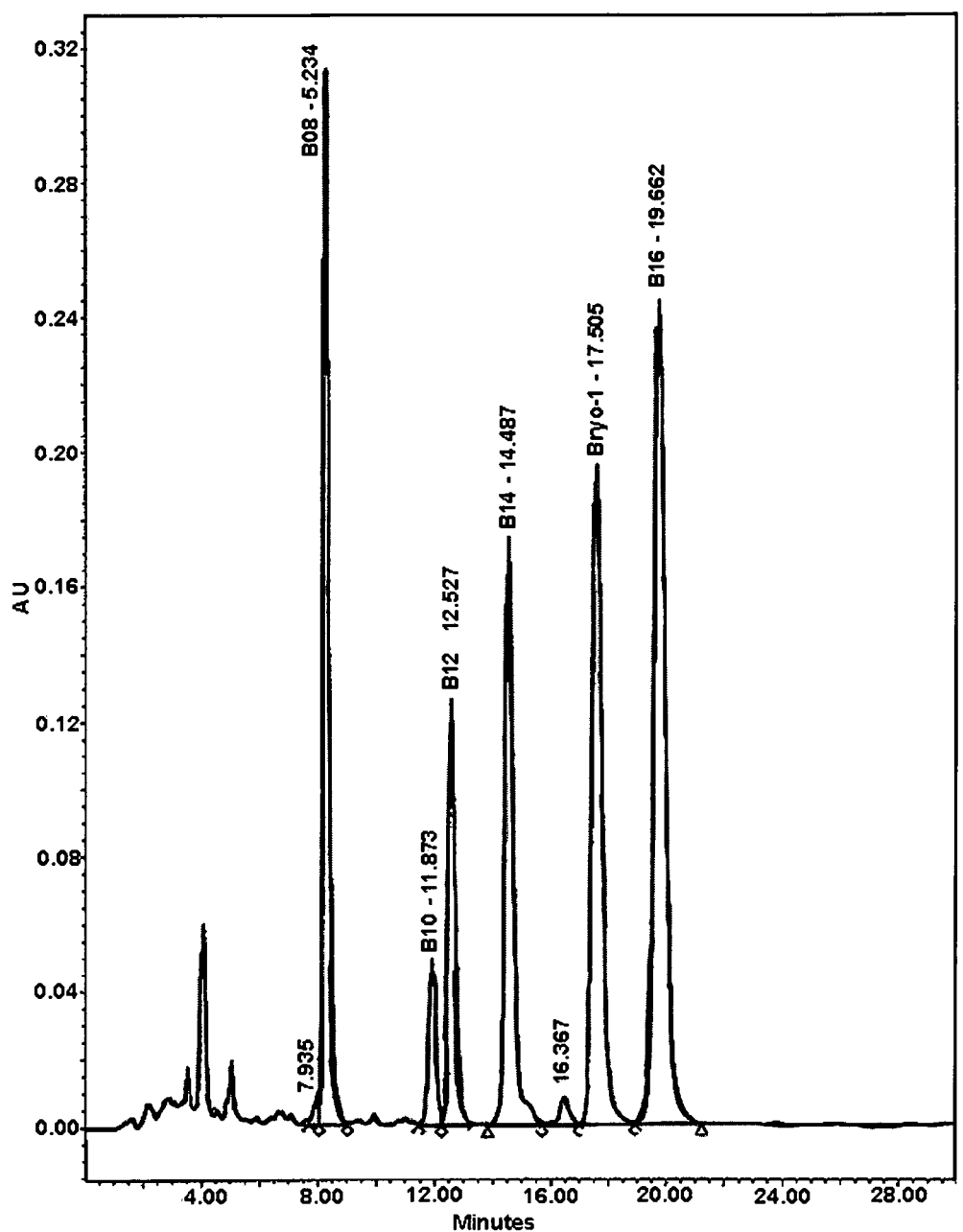
Figure 6: HPLC Chromatogram and Retention Times of Bryoids Mixture monitored at 265 nm

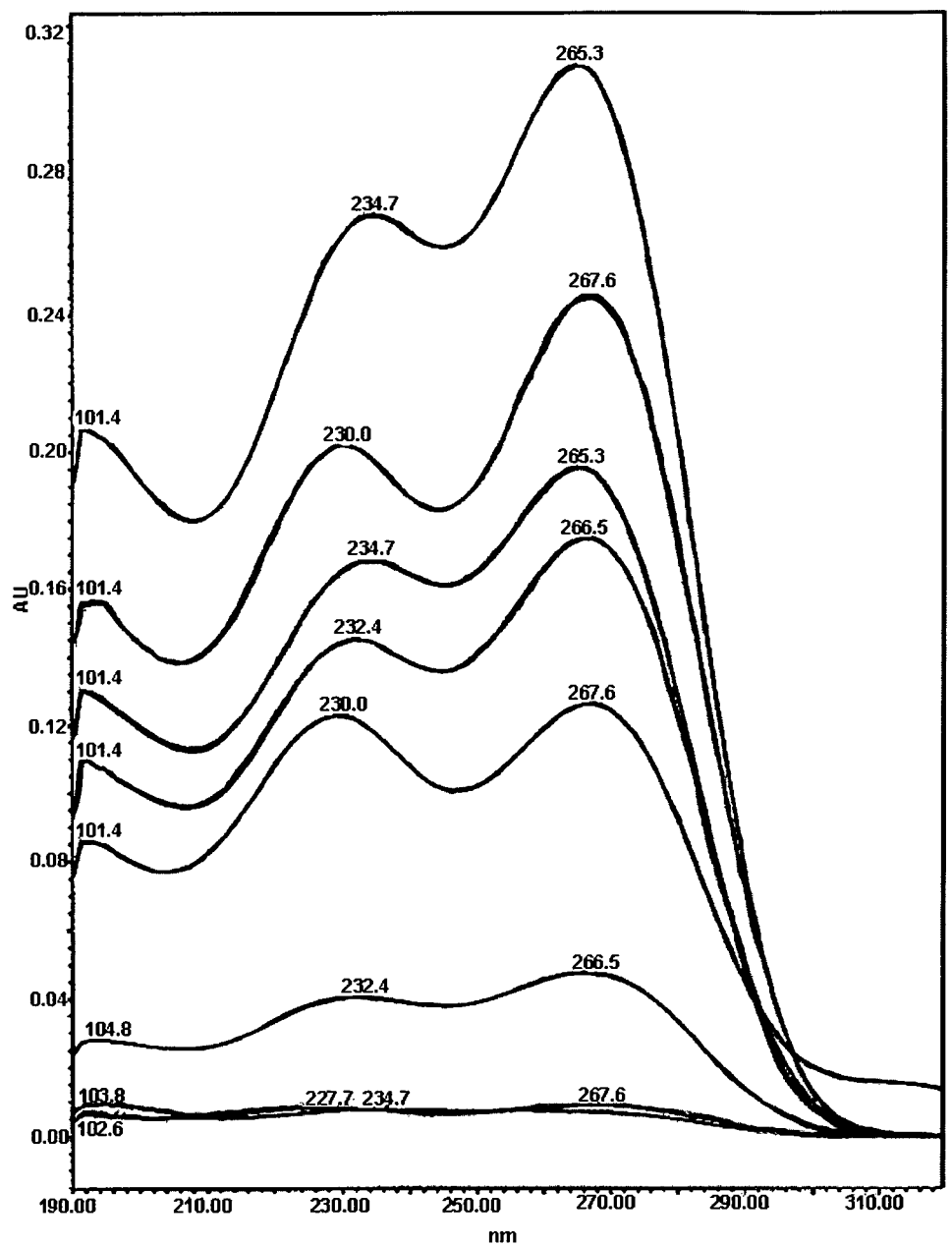
Figure 7: UV Spectra of Different Bryoids at 265 nm

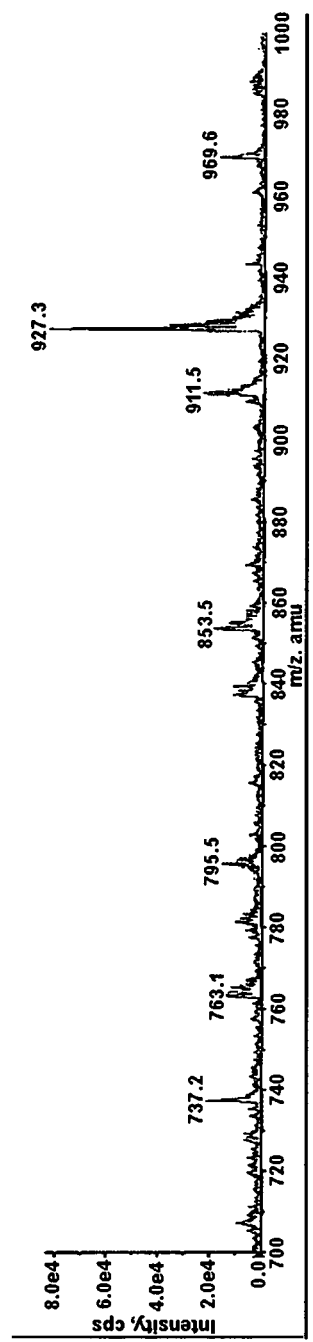
Figure 8-1: Mass Spectrum of Bryostatin-1, Scanning from 700-1000 Amu

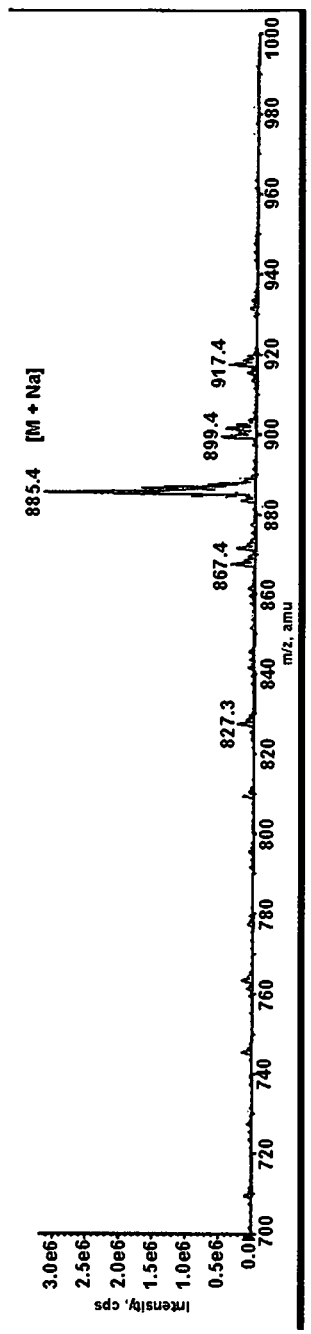
Figure 8-2: Mass Spectrum of Fraction 104 - Bryostatin-2 aka B08, Scanning from 700-1000 Amu

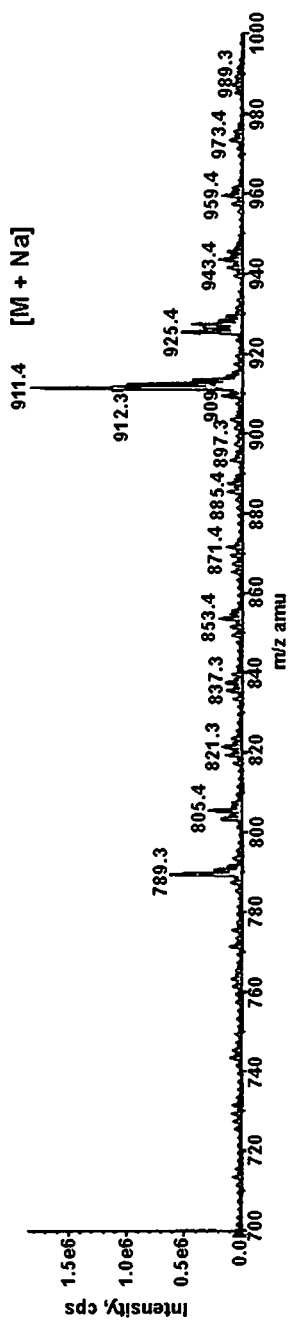
Figure 8-3: Mass Spectrum of Fraction 106- Bryostatin-3 aka B14, Scanning from 700-1000 Amu

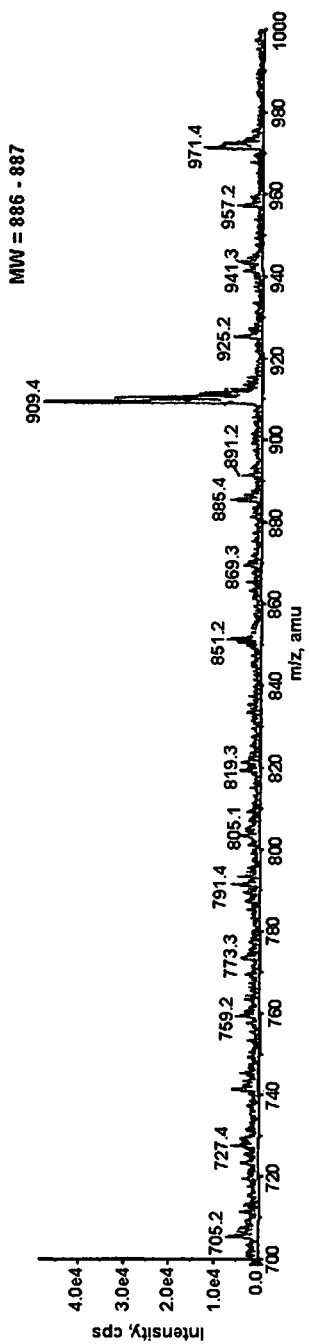
Figure 8-4: Mass Spectrum of Fraction 112 - B16, Scanning from 700-1000 Amu

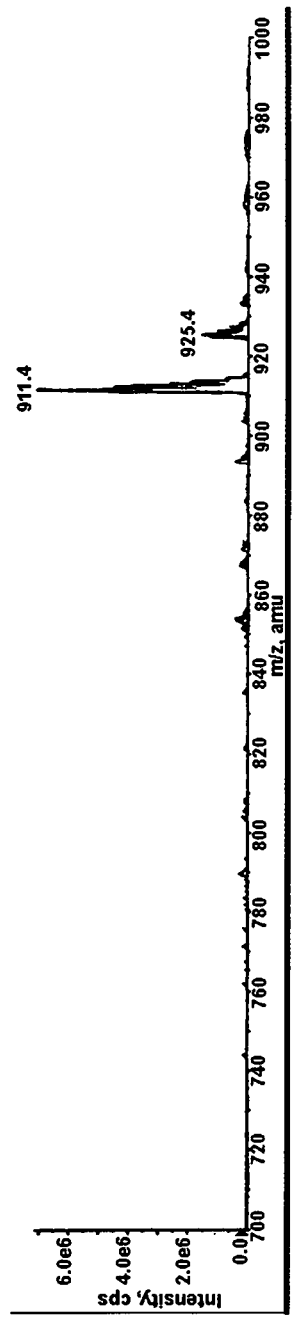
Figure 8-5: Mass Spectrum of Fraction 102-B12 and B14 (Bryostatin-3), scanning from 700-1000 Amu

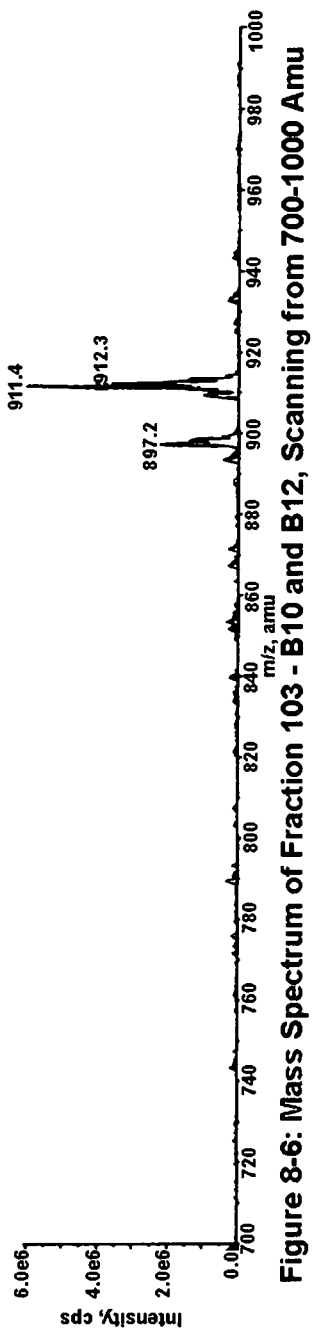
Figure 8-6: Mass Spectrum of Fraction 103 - B10 and B12, Scanning from 700-1000 Amu

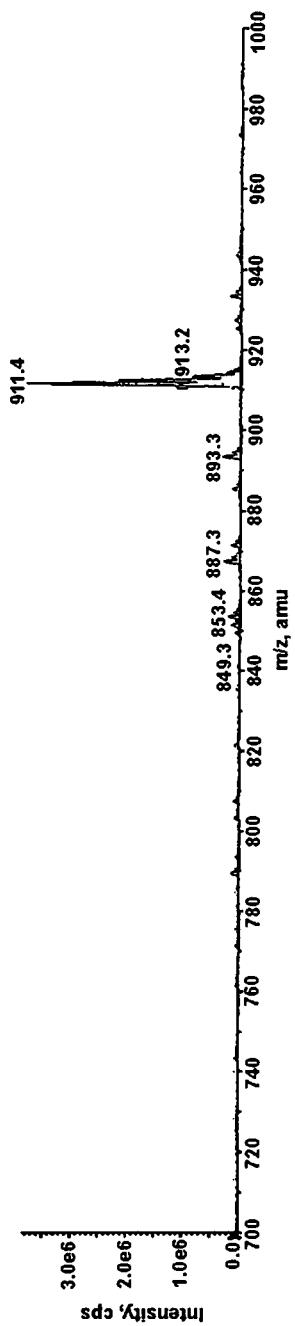
Figure 8-7: Mass Spectrum of Fraction 105 - B12 and B14 (Bryostatin-3), Scanning from 700-1000 Amu

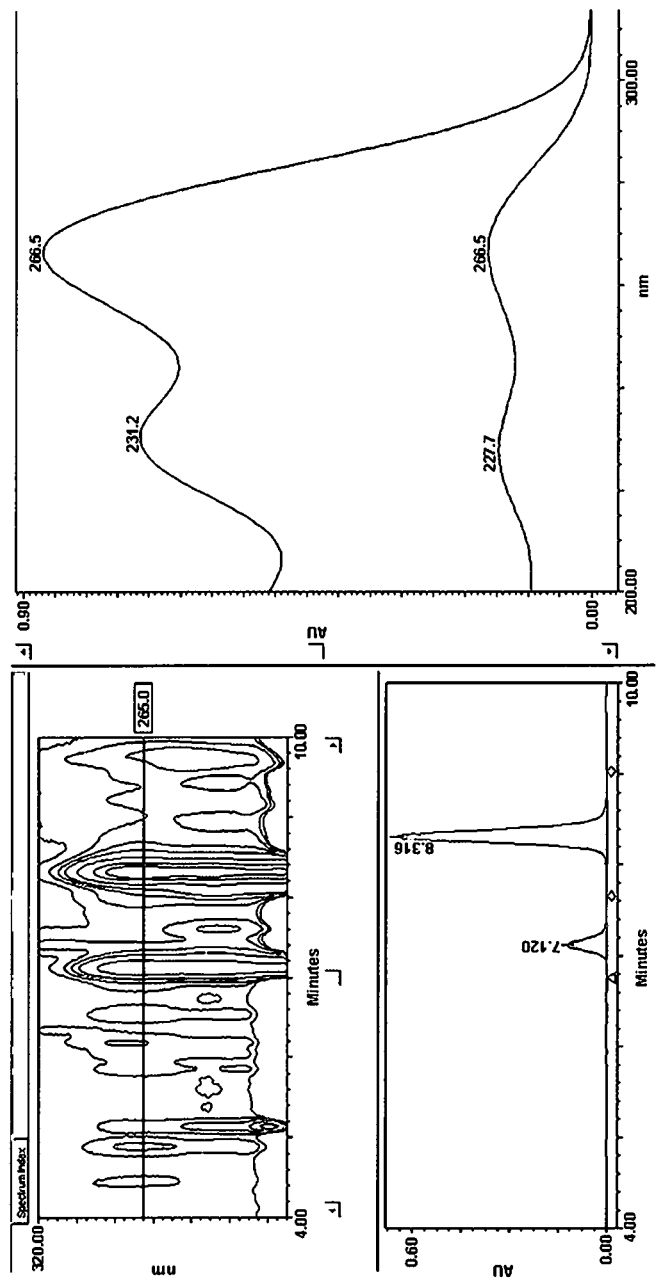
Figure 9: The UV pattern of B14B (RT 7.1 min) and B16 (RT 8.3 min) are similar to the UV pattern of Bryostatin-1

BRYOID COMPOSITIONS, METHODS OF MAKING AND USE THEREOF

RELATED APPLICATION

This application is a continuation of U.S. patent application Ser. No. 14/647,237, filed May 26, 2015, which is a 371 U.S. National Phase of International Application No.: PCT/US2013/72070, filed Nov. 26, 2013, which claims the benefit of U.S. Provisional Patent Application No. 61/730,227, filed Nov. 27, 2012, the entire contents of which are incorporated herein by reference.

STATEMENT REGARDING FEDERAL SPONSORSHIP

The inventions of the present application were developed with Federal sponsorship under National Institute of Aging and National Institutes of Health Grant Number SR44AG034760.

FIELD OF INVENTION

Embodiments of the present invention are directed to compositions having utility as therapeutics in neurodegenerative diseases such as Hutchinson Disease, Parkinson's disease, Down's syndrome and Alzheimer's disease, virus latency diseases such as HIV and Herpes, cancers such as prostate and other amyloid mediated diseases such as glaucoma.

BACKGROUND OF THE INVENTION

Neurodegenerative diseases, such as Alzheimer's disease, Hutchinson's Disease, Parkinson's disease, Kuru, Creutzfeldt-Jakob disease and other spongiform encephalopathies remain major health problems. Currently there are very limited means to treat these diseases. With respect to Alzheimer's, Hutchinson's and Parkinson's diseases, these diseases tend to manifest themselves in older individuals and as the diseases progress; the afflicted individuals are less able to care for themselves. The neurogenerative diseases are associated with the formation of beta amyloid plaques. Bryostatin 1 stimulates the production of certain isoforms of protein kinase C (PKC) that increase the production of alpha-secretase which makes soluble amyloid precursor protein, thus inhibiting the formation of beta amyloid plaques, With respect to cancers such as prostate cancer, Bryostatin 1 inhibits phorbol ester-induced apoptosis in prostate cancer cells by differentially modulating protein kinase C (PKC) delta translocation and preventing PKCdelta-mediated release of tumor necrosis factor-alpha. With respect to virus latency diseases such as HIV latency, Bryostatin-1, as well as many PKC agonists, activates cellular transcription factors such as NF-kB that binds the HIV-1 promoter and regulates its transcriptional activity. In HIV-1 latency the viral promoter is less accessible to cellular transcription factors because nuclear histones surrounding the viral promoter are deacetylated (compacted chromatin). Thus HDAC inhibitors may increase the aceytation of histones (relaxed chromatin) and then transcription factors may have an easy access to the HIV promoter.

Bryoids consist of a family of bryostatins that are complex cyclic macrolide molecules. Bryoids were originally isolated from the marine bryozoan, *Bulgula neritina*, in small quantities. Methods of synthesis are awkward and costly. About twenty Bryoid compositions, known as bryostatins and numbered 1-20, have been identified. Many of the bryoids are known to possess anti-cancer properties.

It would be useful to have new Bryoid compounds that possess high potency and activity.

SUMMARY OF THE INVENTION

Embodiments of the present invention feature a first Bryoid composition having a molecular weight of approximately 896-898 Amu (Mass+Sodium) having a purity of approximately 50% to a crystal forming purity. The first Bryoid composition can also be characterized as a Bryoid compound having a molecular weight of approximately 873-875 Amu (monoisotopic mass) having a purity of approximately 50% and a crystal forming purity. The first Bryoid composition has a measured mass plus sodium of 897.2 Amu and a measured monoisotopic mass of 874.2 Amu. The detailed discussion which follows will refer to this Bryoid as B10.

Embodiments of the present invention feature a second Bryoid composition having a molecular weight of approximately 910-912 Amu (Mass+Sodium) having a purity of approximately 50% to a crystal forming purity. The second Bryoid composition can also be characterized as a Bryoid compound having a molecular weight of approximately 888-890 Amu (monoisotopic mass) having a purity of approximately 50% and a crystal forming purity. The second Bryoid composition has a measured mass plus sodium of 911.5 Amu and a measured monoisotopic mass of 888.9 Amu. The detailed discussion which follows will refer to this Bryoid as B12.

Embodiments of the present invention feature a third Bryoid composition having a molecular weight of approximately 868-870 Amu (Mass+Sodium) having a purity of approximately 50% to a crystal forming purity. The third Bryoid composition can also be characterized as a Bryoid compound having a molecular weight of approximately 846-848 Amu (monoisotopic mass) having a purity of approximately 50% and a crystal forming purity. The third Bryoid composition has a measured mass plus sodium of 869.5 Amu and a measured monoisotopic mass of 846.6 Amu. The detailed discussion which follows will refer to this Bryoid as B14B.

Embodiments of the present invention feature a fourth Bryoid composition having a molecular weight of approximately 895-897 Amu (Mass+Sodium) having a purity of approximately 50% to a crystal forming purity. The fourth Bryoid composition can also be characterized as a Bryoid compound having a molecular weight of approximately 872-874 Amu (monoisotopic mass) having a purity of approximately 50% and a crystal forming purity. The fourth Bryoid composition has a measured mass plus sodium of 895.5 Amu and a measured monoisotopic mass of 872.6 Amu. The detailed discussion which follows will refer to this Bryoid as B14C.

These Bryoid compounds of the present invention have molecular weights that are different than the molecular weights of bryostatins 1-20.

As used herein, crystal forming purity means the composition has a purity which enables the composition to form crystals. Normally, such purity is greater than 90%, and more often greater than 95% purity. Examples presented in this application feature compositions having a purity greater than 99%. Crystal purity would comprise compositions in which no impurities can be detected, but is not so limited.

The Bryoid composition of the present invention has utility in the treatment of Bryoid responsive conditions such as neurodegenerative diseases, cancers and virus latencies. The Bryoid composition of the present invention is highly active modulators of certain isoforms of protein kinase C (PKC) and amyloid precursor protein. The Bryoids, and the Bryoid composition of the present invention, stimulate the production of certain isoforms of protein kinase C (PKC) that increase the production of alpha (alpha) secretase which transforms amyloid precursor protein into soluble forms. Bryoids composition of the present invention exhibit high levels of activity similar to or greater than bryostatin 1.

One embodiment of the present invention is directed to the treatment of a disease such as a neurodegenerative disease, cancer and virus latency responsive to Bryoids, such as Bryostatins 1-20. The method comprises the step of administering an effective amount of at least one bryoid composition selected from the group consisting of the first Bryoid composition, the second Bryoid composition, the third Bryoid composition, and the fourth Bryoid composition.

Embodiments of the present invention further comprise the Bryoid composition selected from the group consisting of the first Bryoid composition, the second Bryoid composition, the third Bryoid composition, and the fourth Bryoid composition in a dosage form for administration to a patient. The dosage form may take many forms including without limitation, intravenous, intraperitoneal, oral dosage forms, such as tablets, gel caps, capsules, oral solutions and suspensions; aerosols, such as spray or mist forming solutions for administration to lungs, or nasal passageways, topical forms such as ointments, lotions, patches and sprays; and other dosage forms known in the art.

A further embodiment of the present invention is directed to a method of making a Bryoid composition selected from the group consisting of the first Bryoid composition, the second Bryoid composition, the third Bryoid, and the fourth Bryoid composition comprising the steps of isolating the a Bryoid composition from a source of Bryoids and purifying the Bryoid composition to a purity of 50% and a crystal forming purity. The source of Bryoids is preferably the marine bryozoan, *Bugula neritina*.

These and other features and advantages of the present invention will be apparent upon viewing the Figures and reading the detailed descriptions that follow.

BRIEF DESCRIPTION OF THE FIGURES

FIG. 1 depicts a high performance liquid chromatography scan of Bryostatin 1;

FIG. 2 depicts a HPLC Chromatogram of *B. neritina* Ethyl Acetate (EA) crude extract;

FIG. 3 depicts a flow chart of purifying steps for Bryostatin-type compositions;

FIG. 4 depicts alpha-secretase activity induced by Bryostatin-1 and other extracts which embody aspects of the present invention;

FIG. 5 depicts a chromatogram of a mixture of Bryoids;

FIG. 6 depicts a chromatogram of a mixture of Bryoids and identifies retention times monitored at 265 nm;

FIG. 7 depicts UV spectra of different Bryoids at 265 nm;

FIG. 8-1 depicts a mass spectrum of Bryostatin 1, scanning from 700-1000 Amu;

FIG. 8-2 depicts a mass spectrum of a fraction with an internal identifications 104 and B08 associated with Bryostatin 2, scanning from 700-1000 Amu;

FIG. 8-3 depicts a mass spectrum of a fraction with internal designations 106 and B14 associated with Bryostatin 3, scanning from 700-1000 Amu;

FIG. 8-4 depicts a mass spectrum of a fraction with internal designations 112 and B16 embodying features of the present invention, scanning from 700-1000 Amu;

FIG. 8-5 depicts a mass spectrum of a fraction with internal designations 102 and B12 and B14 associated with Bryostatin-3, scanning from 700-1000 Amu;

FIG. 8-6 depicts a mass spectrum of a fraction with internal designations 103 and B10 and B12, scanning from 700-1000 Amu;

FIG. 8-7 depicts a mass spectrum of a fraction with internal designations 105 and B12, and B14 associated with Bryostatin-3 scanning from 700-1000 Amu;

FIG. 9 depicts UV spectra of the first Bryoid composition and the second Bryoid composition;

DETAILED DESCRIPTION OF THE INVENTION

Figure 10:
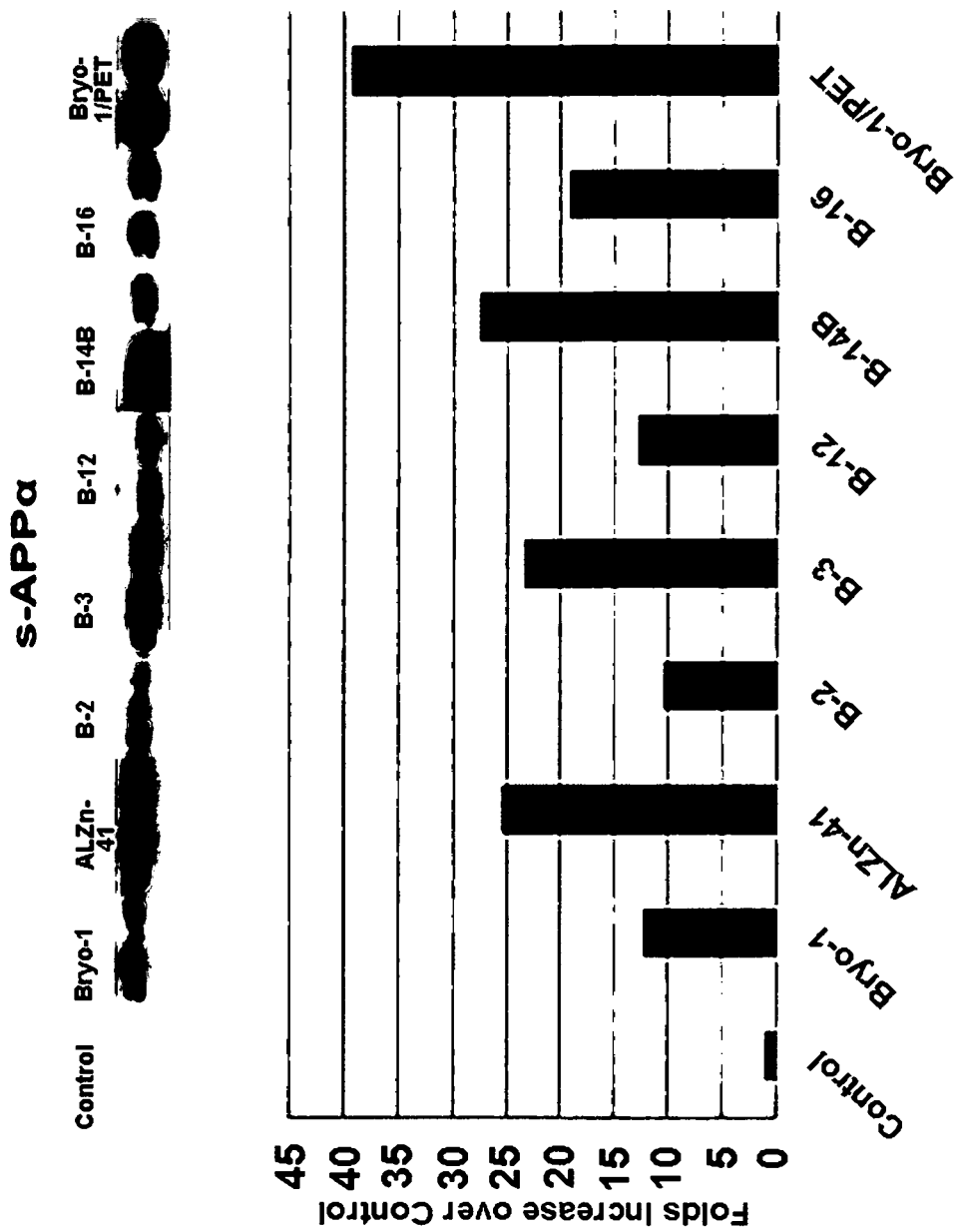
FIG. 10 depicts the effect of Bryostatin-1 and different Bryoids at $10^{-9}$M on alpha-secretase activity in SHSY-5Y neuroblastoma cells.

Embodiments of the present invention will now be described with respect to a Bryoid composition selected from the group consisting of the first Bryoid composition (sometimes referred to as B10), the second Bryoid composition (sometimes referred to as B12), the third Bryoid composition (sometimes referred to as B14B), the fourth Bryoid composition (sometimes referred to as B14C). These Bryoid compounds of the present invention have molecular weights that are different than the molecular weights of Bryostatins 1-20, with the exception of B12 which appears to be a stereoisomer of Bryostatin 3.

*Bugula neritina* was fractionated to produce Bryostatin fractions (Bryoids) and isolate individual Bryoids.

HPLC Analysis:

Bryostatin-1 was analyzed by HPLC using a 15 cm 5 micron Phenomenex Luna PFP (2) column (UPS Packing L43) and a mobile phase of 60% acetonitrile acidified with 50 microliters of 85% $H_3PO_4$ per liter. The flow rate was set to 1.0 mL per minute and the column temperature was set at 30° C. A Waters Millennium system incorporating a Model 996 photodiode array detector was used to generate the chromatographic scans (FIG. 1). Bryostatin-1 was monitored at 265 nm, and contour plots were simultaneously reported from 195 nm to 345 nm.

Bryostatin-1 Manufacturing and Characterization:

In the first two steps, Bryostatins are extracted from wet *Bugula neritina* with organic solvents including isopropanol, methanol, ethyl acetate and water followed by silica chromatography using mobile phases consisting of hexane/ methylene chloride and ethyl acetate/methanol or alternatively extracted from washed, dried and milled *Bugula neritina* with SuperFluids™ (near-critical and supercritical fluids with or without cosolvents) carbon dioxide and methanol and partially purified by SuperFluids™ silica chromatography with carbon dioxide and methanol (Castor, 1998, 2001).

The third step is a segmentation chromatography step on a CG71 polymeric resin (Rohm-Haas) with a mobile phase consisting of methanol and water that improves the purity of Bryostatin-1 to 60-70%. The fourth step utilizes a segmentation chromatographic method using two semi-prep HPLC C18 columns (Baker Scientific, Phenomenex) with a mobile phase consisting of acetonitrile and water to improve the Bryostatin-1 purity to >95%. The fifth step utilizes crystallization with acetonitrile and water to purify Bryostatin-1 to >98.5%.

The identity of the Bryostatin-1 product was confirmed by Ultra Violet (UV) spectra as well as High Performance Liquid Chromatography (HPLC) retention times versus those of standards provided by the U.S. National Cancer Institute (NCI), National Institutes of Health (NIH), Bethesda, Md. The identity of the Bryostatin-1 product was also confirmed independently by Mass Spectral (MS) data as well as by Elemental Analysis, Proton and Carbon Nuclear Magnetic Resonance (NMR), Infra Red (IR) spectroscopy, Differential Scanning calorimetry (DSC) and Melting Point.

Purification of Bryostatin-1 to 99.64% CP

Purification Procedure and Results:

An ethyl acetate extract of *B. neritina* (Sample C-021519#7), provided by the National Cancer Institute (NCI), was used as the starting raw materials. A total of ~57 g of the EA extract was dissolved in dichloromethane (DCM) and assayed to determine presence of Bryostatin-1 and other Bryoids. Turning now to FIG. 2, a HPLC Chromatogram of *B. neritina* EA crude extract is depicted. Labeled arrows indicate internal designations for Bryostatin-like compounds, which include B10, B12, and Bryostatin 3 (B16), and Bryostatin-2 (Bryn-2) and Bryostatin-3 (Bryo-3). Bryostatin-1 (Bryo-1) elutes at 24.2 min. The designation B10 is the bryoid corresponding to the first bryoid of the present invention. The designation of B14 will lead to the third and fourth Bryoids of the present invention.

Bryostatin-1 was purified from *B. neritina* EA crude extracts using various chromatography resins as shown in FIG. 3. The initial steps (Step 1 and Step 2) were performed on Silica gel Active (100-200 µm), and the sample eluted with increasing concentrations of ethyl acetate in DCM. The silica purification steps are useful in removing some of the colored components from the EA crude extract, the non-polar compounds (eluting at end of chromatographic run, FIG. 3), and eliminating the majority of the B16 peak.

Next, fractions containing Bryostatin-1 were purified on Amberchrom CG71, which allowed for the elution of Bryostatin-like compounds with acidified methanol and water. This resin helps minimize the use of chlorinated solvents that are harmful to the environment. CG71 purification step removes the 'X5' peak eluting before Bryostatin-1. It also served to minimize the impurities right before Bryostatin-1, mainly B16.

Subsequent purification was performed using a combination of Amicon C18 40 µm resin and two prep-C18 columns (2.5×2.5 cm, 10 µm column) This step allowed for the further separation of B12 and Bryo-3 from Bryostatin-1, though there was still the presence of the 'x5' peak at the shoulder of Bryostatin-1. Final crystallization step led to the purification of Bryostatin-1 to >99% chromatography purity (CP), with a 69% recovery from crude extract.

HPLC Monitoring:

During each purification step outlined in FIG. 3, Bryostatin-1 was monitored on a Luna C18(2) column (250×4.6 mm, 10 µm). Elution was performed at 80% acetonitrile acidified with phosphoric acid (ACNP) in an isocratic mode at a 2 mL/min flow rate. Column temperature was set at 30° C.

Bryostatin-Like Compounds (Bryoids)

*Bugula neritina* was fractionated to produce Bryostatin fractions (Bryoids) that could serve as alternatives to Bryostatin-1. These fractions were purified and sent to LSU for in vitro analysis (Table 1).

TABLE 1

Amount (in mg) of each Bryoid in the Fractions as determined by HPLC[1]

| Fraction | Sample | B08 | B10 | B12 | B14 | Bryo-1 | B16 | % CP |
|---|---|---|---|---|---|---|---|---|
| A: 101 | B157 165 mL | | | | | 88.8 | | 97.5 |
| B: 102 | B154 | | | 30.5 | 101.1 | 4.2 | | 74.4 |
| C: 103 | B158 B12 350 mL | | 60.4 | 100.8 | 6.7 | | | 49.3 |
| D: 104 | Bryo-2 | 100.9 | | | | | | 94.4 |
| E: 105 | Bryo-AB | | | | 99.8 | 53.7 | | 64.5 |
| F: 106 | Bryo-3 | | | | 98.3 | | 12.1 | 72.1 |
| G: 112 | B16 APH 100311 | | | | | | 99.5 | 97.5 |

CP corresponds to Bryoid in bold

Efficacy of Bryostatin-1 Analogues (Bryoids) in Induction of s-APPα Secretion:

The efficacy of several Bryostatin-1 analogues (Bryoids) in induction of s-APPα secretion is shown in FIG. 4. Except Fraction D, they all induced significant release of s-APPα compared to Bryostatin-1. The best alternative fraction to Bryostatin-1 is analogue E which corresponds to the designation B16, which was identified as Bryostatin 3. Bioactivity went in order from Fraction E (105)>G (112), F (106), C (103)>A (101), B (102)>D (104).

From the preliminary data, it appears that B12 or B14 can be significantly more bioactive than Bryostatin-1. Since most fractions contain two or more Bryoids, it is difficult to determine which one is responsible for the bioactivity except for Fraction G, which contains B16 at >97.5% CP. The first bryoid composition of the present invention, B10, has significantly higher activity than Bryostatin-1, and it poses another potential alternative Bryoid as a therapeutic.

HPLC Standardization:

Turning now to FIG. 5, which depicts a high performance liquid chromatograph of a bryoid mixture at 265 nm, various Bryoids are present in the *B. neritina* EA crude extract.

The mixture of the Bryoids (B09, B10, B12, B14C, B14B, B16, Bryostatin-1, Bryostatin-2, and Bryostatin-3) were standardized for the purpose of identification (based on retention time) and subsequent purification of each Bryoid. A chromatogram depicting the results of high performance liquid chromatography purification is depicted in FIG. 6. These Bryoids contain similar UV patterns as Bryostatin-1 with a maximum wavelength at 265 nm as shown in FIG. 7 which depicts UV spectra of different bryoid at 265 nm.

Identification of each Bryoid was attempted on UV-HPLC and LC/MS/MS using known standards and/or comparing to known masses in the literature. This is important as previous preliminary in vitro experiments (described above) have shown that these Bryoids may induce s-APPα secretion at equal or even greater percentages than is observed for Bryostatin-1.

Preliminary Characterization Based on LC/MS/MS

Characterization of the different Bryoids was performed using an LC/MS/MS API 2000 system equipped with a Shimadzu HPLC system. Q1 scan parameters were optimized for Bryostatin-1 m/z 427 [M+Na] (FIG. 8-1), scanning from 700 to 1000 amu. Mass spectrum scans of other fractions are presented in FIGS. 8-2 through 8-7. A total of seven fractions were analyzed, which included individual Bryoids and mixture of Bryoids (Table 2).

TABLE 2

Bryostatin Analogue for Each Fraction Based on Mass Match

| Bryoid | Mass + Na | Mass [M] | Bryostatin Match Based on Mass |
|---|---|---|---|
| Fraction 101: Bryo-1 | 927.3 | 904.3 | Bryostatin-1 |
| Fraction 102: B12 and B14 (Bryo-3) | 911.4 | 888.4 | Bryostatin-3 |
|  | 925.4 | 902.4 | None |
| Fraction 103: B10 and B12 | 911.4 | 888.4 | Bryostatin-3 |
|  | 897.2 | 874.2 | None |
| Fraction 104: Bryo-2 | 885.4 | 862.4 | Bryostatin-2 |
| Fraction 105: B12 and Bryo-3 | 911.4 | 888.4 | Bryostatin-3 |
| Fraction 106: Bryo-3 | 911.4 | 888.4 | Bryostatin-3 |
| Fraction 112: B16 | 909.4 | 886.4 | None (tentatively identified as Bryostatin-3) |

Discussion:

The LC/MS/MS data observed for Bryostatin-1 shows a peak at 927 Amu, which corresponds to the [M+NA], and what has been reported in the literature (Manning et al., 2005). Mass spectral data on Bryostatin-1 to 18 are summarized in Table 3. Based on the LC/MS/MS analysis performed, Fractions 104 and Fraction 106 were confirmed as Bryostatin-2 (863 Amu) and Bryostatin-3 (889 Amu), receptively.

Fraction 112 showed that B16 mass does not match any Bryoids reported in the literature. Fractions 102, 103, and 105 showed a mass peak identical to what was observed for Bryostatin-3. Both Fraction 102 and 105 contain Bryo-3 in their mixture, which would explain the 911 peak observed in the LC/MS/MS. It is unclear why 911 Amu is seen in Fraction 103; this indicates that B12 may have the same mass as Bryostatin-3 (889 Amu). This is supported by the fact that Fraction 105, containing both B12 and Bryo-3, only showed a peak at 911 Amu. The 897 peak observed in Fraction 103 could correspond to B10, though it does not match any of the Bryostatin masses reported in the literature. The peak at 925 Amu in Fraction 102 is also observed in Fraction 106.

TABLE 3

Mass Spectral Information on Bryostatin-1 to 18 (Manning et al., 2005)

| Bryo. # | Monoisotopic mass | M. M. + (Na$^+$): 22.9892 | M. M. ± (H$_2$): 2.0156 | Group R1 monoisotopic mass (attached) | Group R2 monoisotopic mass (attached) | Empirical formula |
|---|---|---|---|---|---|---|
| 1 | 904.4456 | 927.4348 | 902.4300 / 906.4613 | 59.0133: $CH_3COO$ | 139.0759: $CH_3(CH_2)_2(CH)_4COO$ | $C_{47}H_{68}O_{17}$ |
| 2 | 862.4350 | 885.4243 | 860.4194 / 864.4507 | 17.0027: OH | 139.0759: $CH_3(CH_2)_2(CH)_4COO$ | $C_{45}H_{66}O_{16}$ |
| 3 | 888.4143 | 911.4035 | 886.3987 / 890.4300 | 59.0133: $CH_3COO$ | 139.0759: $CH_3(CH_2)_2(CH)_4COO$ | $C_{46}H_{64}O_{17}$ |
| 4 | 894.4613 | 917.4505 | 892.4456 / 896.4769 | 101.0602: $(CH_3)_2CHCH_2COO$ | 87.0446: $CH_3(CH_2)_2COO$ | $C_{46}H_{70}O_{17}$ |
| 5 | 866.4300 | 889.4192 | 864.4143 / 868.4456 | 101.0602: $(CH_3)_2CHCH_2COO$ | 59.0133: $CH_3COO$ | $C_{44}H_{66}O_{17}$ |
| 6 | 852.4143 | 875.4035 | 850.3987 / 854.4300 | 87.0446: $CH_3(CH_2)_2COO$ | 59.0133: $CH_3COO$ | $C_{43}H_{64}O_{17}$ |
| 7 | 824.3830 | 847.3722 | 822.3674 / 826.3987 | 59.0133: $CH_3COO$ | 59.0133: $CH_3COO$ | $C_{41}H_{60}O_{17}$ |
| 8 | 880.4456 | 903.4348 | 878.4300 / 882.4613 | 87.0446: $CH_3(CH_2)_2COO$ | 87.0446: $CH_3(CH_2)_2COO$ | $C_{45}H_{68}O_{17}$ |
| 9 | 852.4143 | 875.4035 | 850.3987 / 854.4300 | 87.0446: $CH_3(CH_2)_2COO$ | 59.0133: $CH_3COO$ | $C_{43}H_{64}O_{17}$ |
| 10 | 808.4245 | 831.4137 | 806.4088 / 810.4401 | 101.0602: $(CH_3)_3CCOO$ | 1.0078: H | $C_{42}H_{64}O_{15}$ |
| 11 | 766.3775 | 789.3667 | 764.3619 / 768.3932 | 59.0133: $CH_3COO$ | 1.0078: H | $C_{39}H_{58}O_{15}$ |
| 12 | 932.4769 | 955.4661 | 930.4613 / 934.4926 | 87.0446: $CH_3(CH_2)_2COO$ | 139.0759: $CH_3(CH_2)_2(CH)_4COO$ | $C_{49}H_{72}O_{17}$ |
| 13 | 794.4088 | 817.3980 | 792.3932 / 796.4245 | 87.0446: $CH_3(CH_2)_2COO$ | 1.0078: H | $C_{41}H_{62}O_{15}$ |
| 14 | 824.4194 | 847.4086 | 822.4037 / 826.4350 | 101.0602: $(CH_3)_3CCOO$ | 17.0027: OH | $C_{42}H_{64}O_{16}$ |
| 15 | 920.4405 | 943.4297 | 918.4249 / 922.4562 | 59.0133: $CH_3COO$ | 155.0708: $CH_3CH_2CHOH(CH)_4$—$COO$ | $C_{47}H_{68}O_{18}$ |
| 16 | 790.4139 | 813.4031 | 788.3983 / 792.4296 | 101.0602: $(CH_3)_3CCOO$ | 1.0078: H | $C_{42}H_{62}O_{14}$ |
| 17 | 790.4139 | 813.4031 | 788.3983 / 792.4296 | 101.0602: $(CH_3)_3CCOO$ | 1.0078: H | $C_{42}H_{62}O_{14}$ |
| 18 | 808.4245 | 831.4137 | 806.4088 / 810.4401 | 101.0602: $(CH_3)_3CCOO$ | 1.0078: H | $C_{42}H_{64}O_{15}$ |

Isolation of Bryostatin Analogues: B16 (98.5% CP) and B14B (93.4% CP)

Bryoid-like compounds, B16 and B14B, were purified from side-cuts collected from previous Bryostatin-1 purifications, and had been stored at 4° C. The bryoids' UV-spectra are identical to that of Bryostatin-1 (FIG. 9).

HPLC Monitoring:

During purification, B16 and B14B were monitored on a Luna C18(2) column (250×4.6 mm, 10 µm). Elution was performed at 80% ACNP (acetonitrile acidified with phosphoric acid) isocratic mode, at a 2 mL/min flow rate. Column temperature was set at 30° C.

Purification Procedure and Results:

Fractions containing B16 and B14B were purified using two prep-C18 columns (2.5×2.5 cm, 10 µm) and a semi-prep PFP column. Purification was performed with step-gradient using increasing concentrations of ACNP. Elution was monitored until each Bryoid was located mainly on individual columns. Columns were stripped using a fast gradient with ACNP, and fractions were assayed to determine concentration of each peak.

Bryoids B16 and B14 B can be separated successfully using the described column system. The use of both C18 and PFP column is necessary for the separation of B16 from B14B, and partial purification of B14B from B14C. Peak labeled B14C is another bryoid that co-elutes with B14B, and can be better monitored when analyzed at 70% ACNP. Crystallization of both B16 and B14B/C was possible by addition of MeOH to the Bryoid-containing fractions. A total of 212 mg of B16 crystals with 98.5% CP were collected. A total of 108 mg of B14B/C at 93.4% CP was recovered and stored for future purification. B14B/C was subsequently separated into B14B and B14C. The purified Bryoids were re-analyzed by LC/MS/MS. The results are summarized in Table 4.

TABLE 4

LC/MS/MS Analysis of Purified Bryostatin Analogues for Each Fraction Based on Mass Match

| Bryoid | Mass + Na | Mass [M] | Bryostatin Match Based on Mass |
|---|---|---|---|
| Bryostatin-1 | 927.3 | 904.3 | Bryostatin-1 |
| Bryostatin-2 | 885.4 | 862.4 | Bryostatin-2 |
| Bryostatin-3 | 911.4 | 888.4 | Bryostatin-3 |
| B16 | 909.4 | 886.4 | None |
| B10 | 897.4 | 874.4 | None |
| B12 | 911.5 | 888.9 | Bryostatin-3 Isomer |
| B14B | 869.5 | 846.6 | None |
| B14C | 895.5 | 872.6 | None |

Biological Activities of Purified Bryoids:

Purified Bryoids at $10^{-9}$M are shown to increase alpha-secretase activity in SHSY-5Y neuroblastoma cells in FIG. 10. B3, B14B and B16 are shown to improve the production of alpha-secretase over Bryostatin-1.

Figure 11:
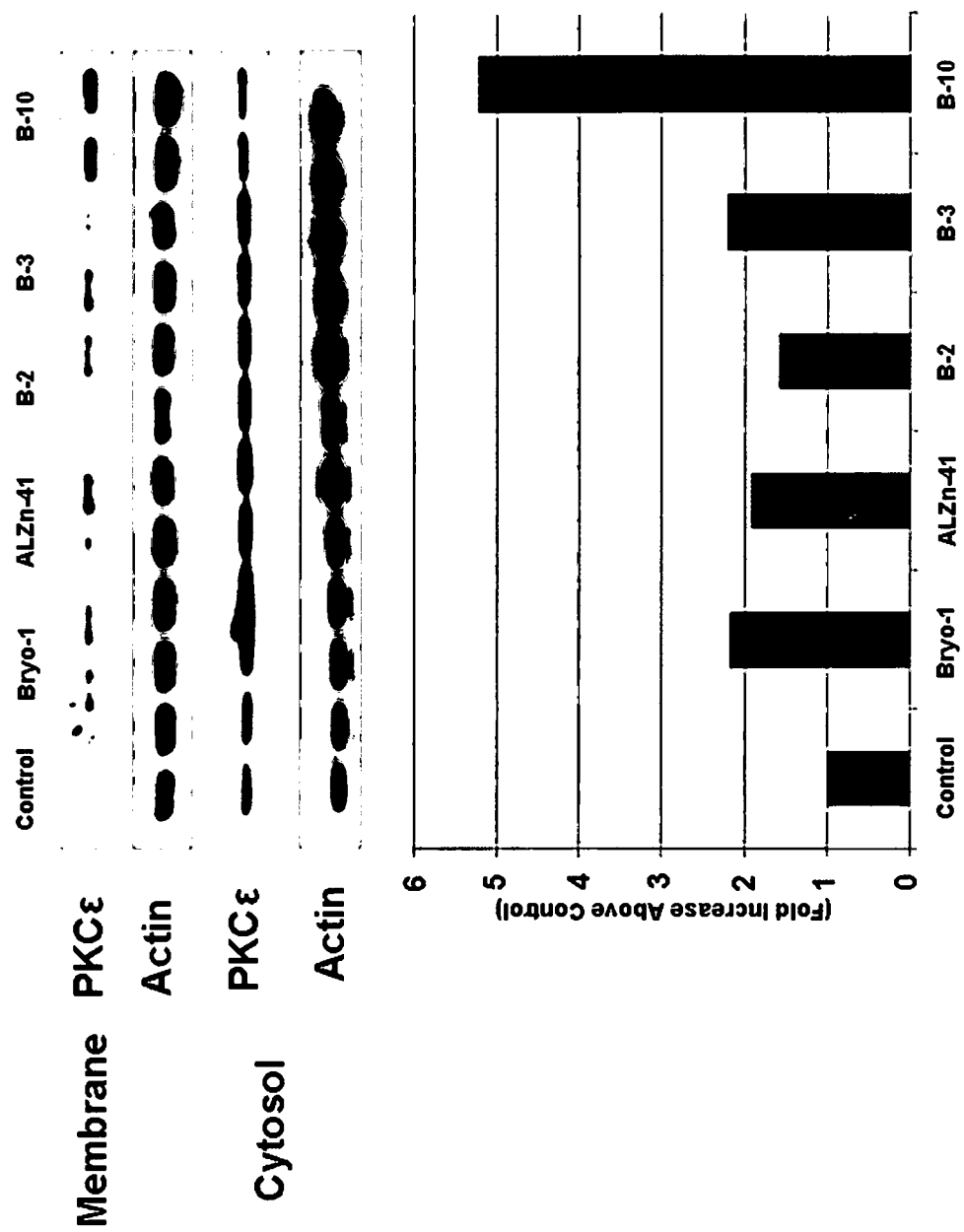
FIG. 11 depicts the effect of Bryostatin-1 and different Bryoids at $10^{-9}$M on PKC-epsilon activity in SHSY-5Y neuroblastoma cells.
Figure 12:
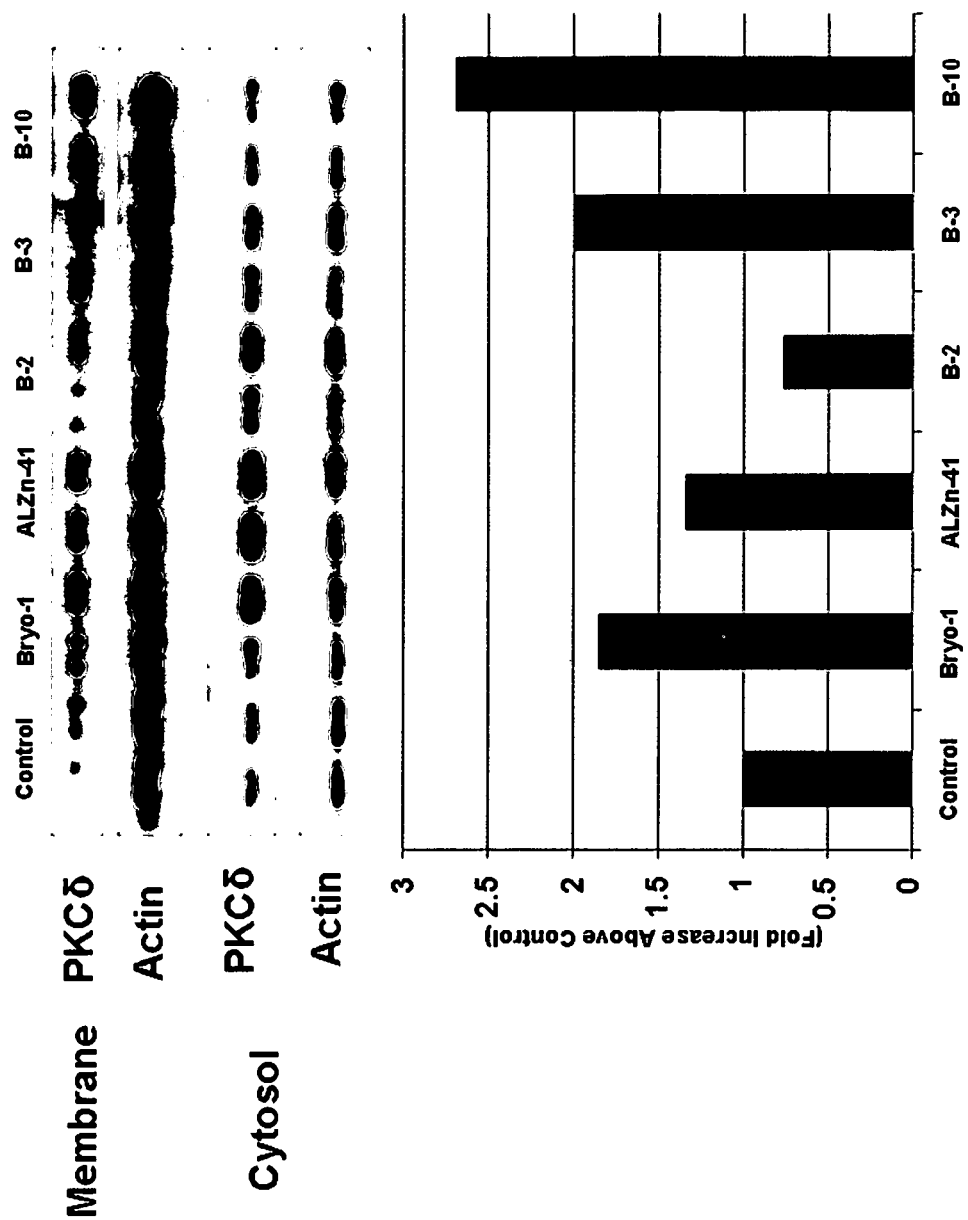
FIG. 12 depicts the effect of Bryostatin-1 and different Bryoids at $10^{-9}$M on PKC-delta activity in SHSY-5Y neuroblastoma cells.
Figure 13:
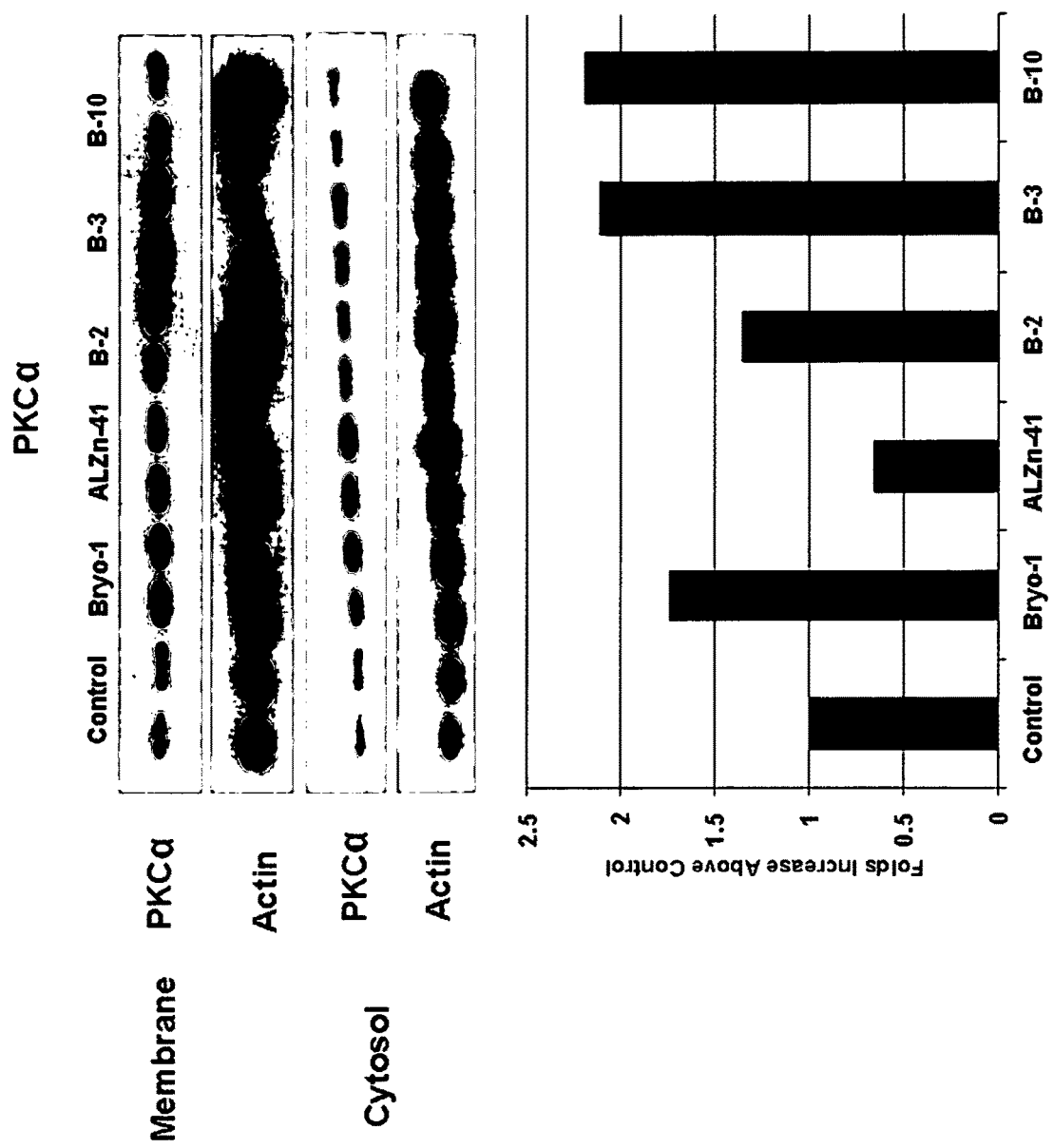
FIG. 13 depicts the effect of Bryostatin-1 and different Bryoids at $10^{-9}$M on PKC-alpha activity in SHSY-5Y neuroblastoma cells.

B10 is shown to improve the production of PKC-epsilon over Bryostatin-1 in FIG. 11. B10 is shown to improve the production of PKC-delta over Bryostatin-1 in FIG. 12. B10 is shown to improve the production of PKC-alpha over Bryostatin-1 in FIG. 13.

Figure 14:
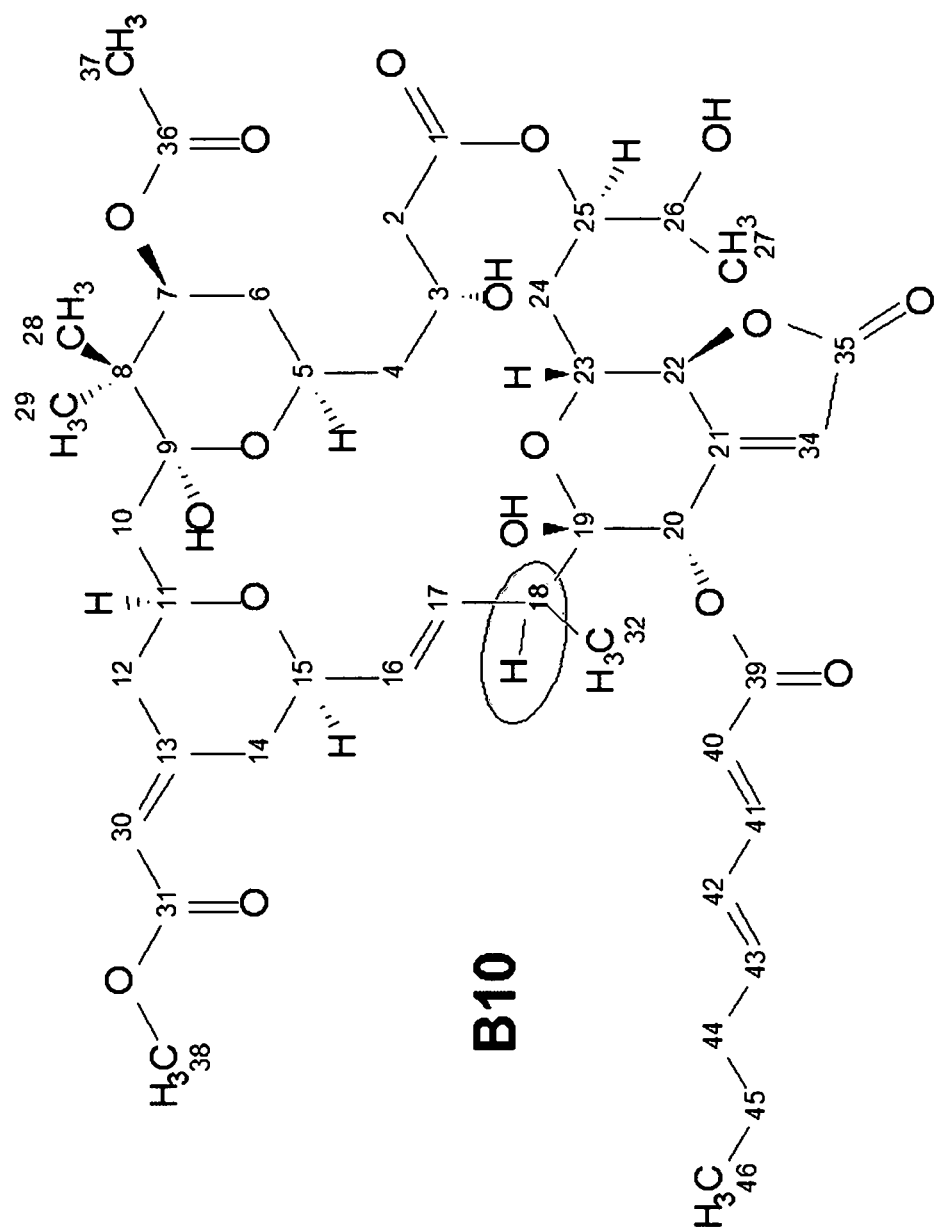
FIG. 14 depicts the proposed structure of a first Bryoid.

NMR and Structural Characterization:

The three variants were compared by to bryostatin 1 and bryostatin 3 by their NMR $^1$H and $^{13}$C resonances and connectivities (HSQC and HMBC spectra). All three variants distinctly had the ring closure at C22 of bryostatin 3, and similar R1 and R3 sidechains (the OAc and the 8-carbon 2,4-ene). The variations, relative to bryostatin 3, were:

B10: NMR showed loss of one methyl group from C18, matching the mass difference: Predicted $C_{45}H_{62}O_{17}$=874.4 (monoisotopic); obs B10 874.4. The putative structure of B10 is depicted in FIG. 14.

Figure 15:
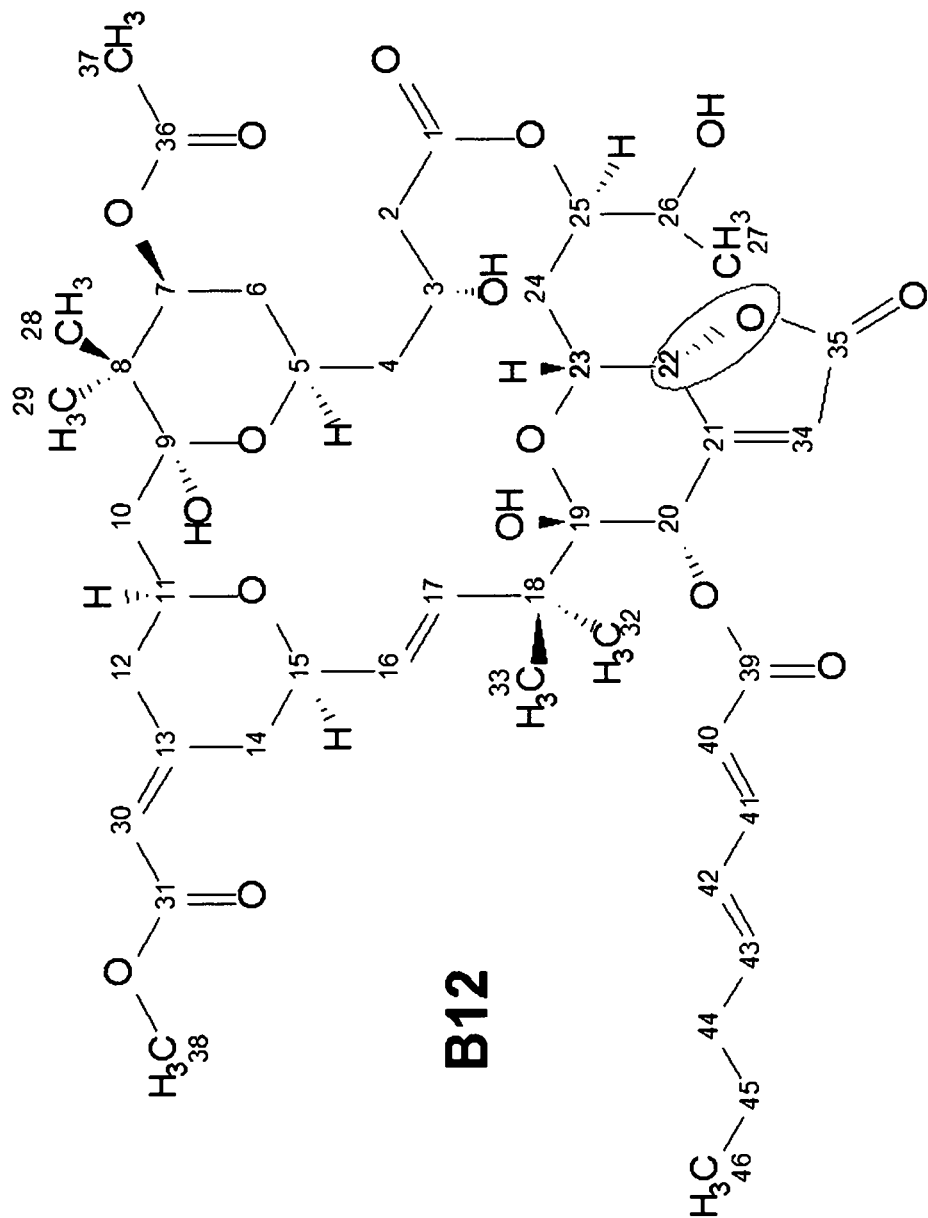
FIG. 15 depicts the proposed structure of a second Bryoid.

B12 appears to be a stereoisomer: a number of protons in the vicinity of the 19-24 ring have modest changes in chemical shift; but the connectivities show the same covalent structure as bryostatin 3, and it has the same mass as bryostatin 3 ($C_{46}H_{64}O_{17}$=888.4). The most likely site would be at C22, if the mechanism of ring closure was not perfectly stereoselective. Inversion at adjacent sites (19, 20, or 23) could also explain the NMR changes, although these variations are not seen among the other bryostatins. The putative structure for B12 is depicted in FIG. 15.

In B16, the 26-OH has become a ketone. This change accounts for the 2 Da observed mass difference between B16 ($C_{46}H_{62}O_{17}$=886.4) and Bryo-3 (888.4). A bryostatin-3 26-ketone is known (Schaufelberger 1991).

Figure 16:
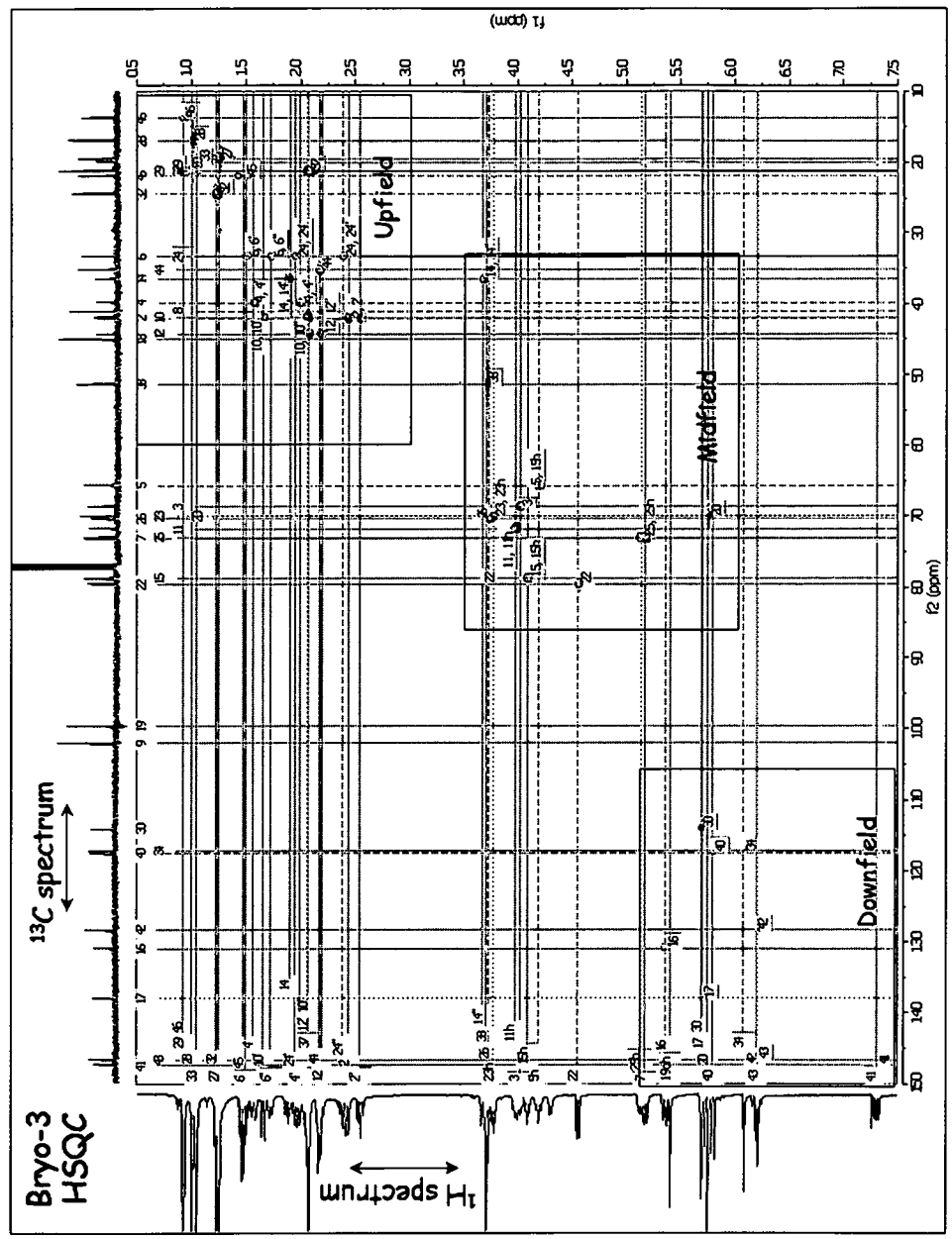
FIG. 16 depicts the NMR spectra of Bryostatin-3.
Figure 17:
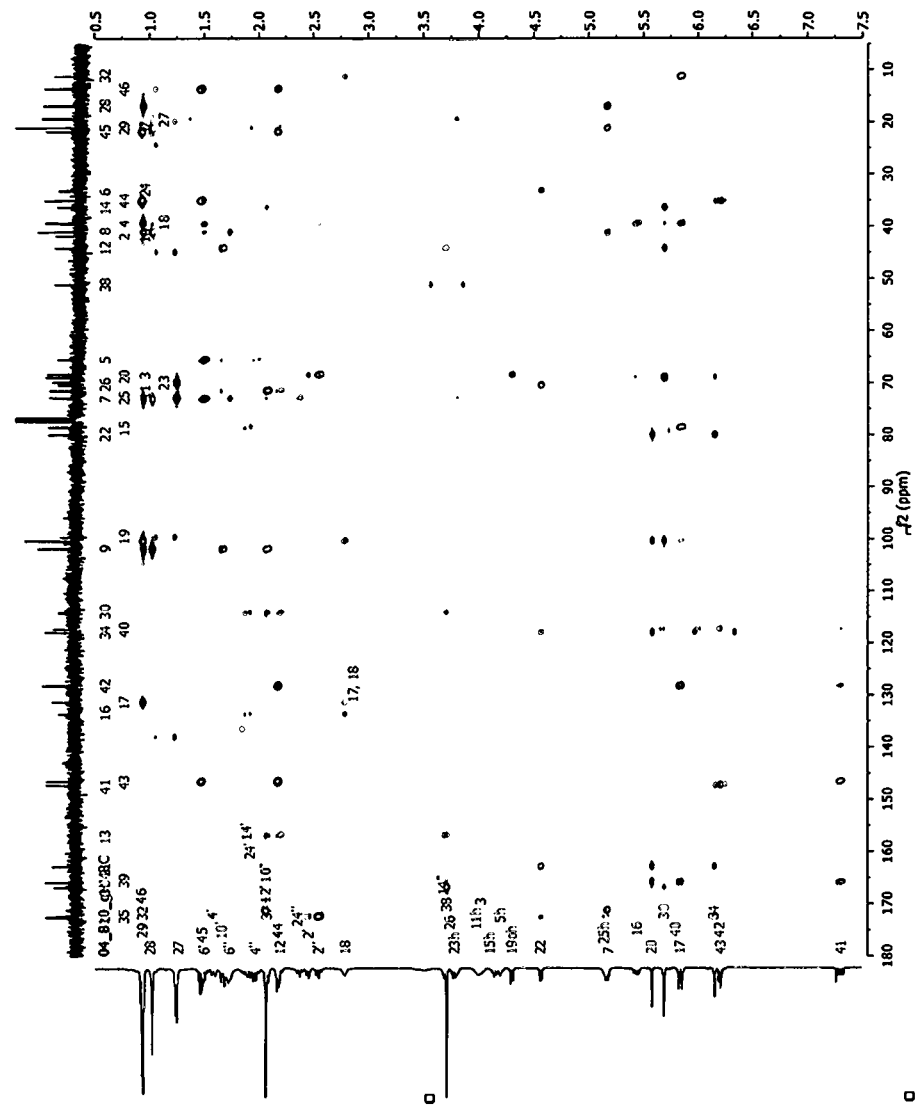
FIG. 17 depicts the NMR spectra of the first Bryoid; and,
FIG. 18 depicts the NMR spectra of the second Bryoid.
Figure 18:
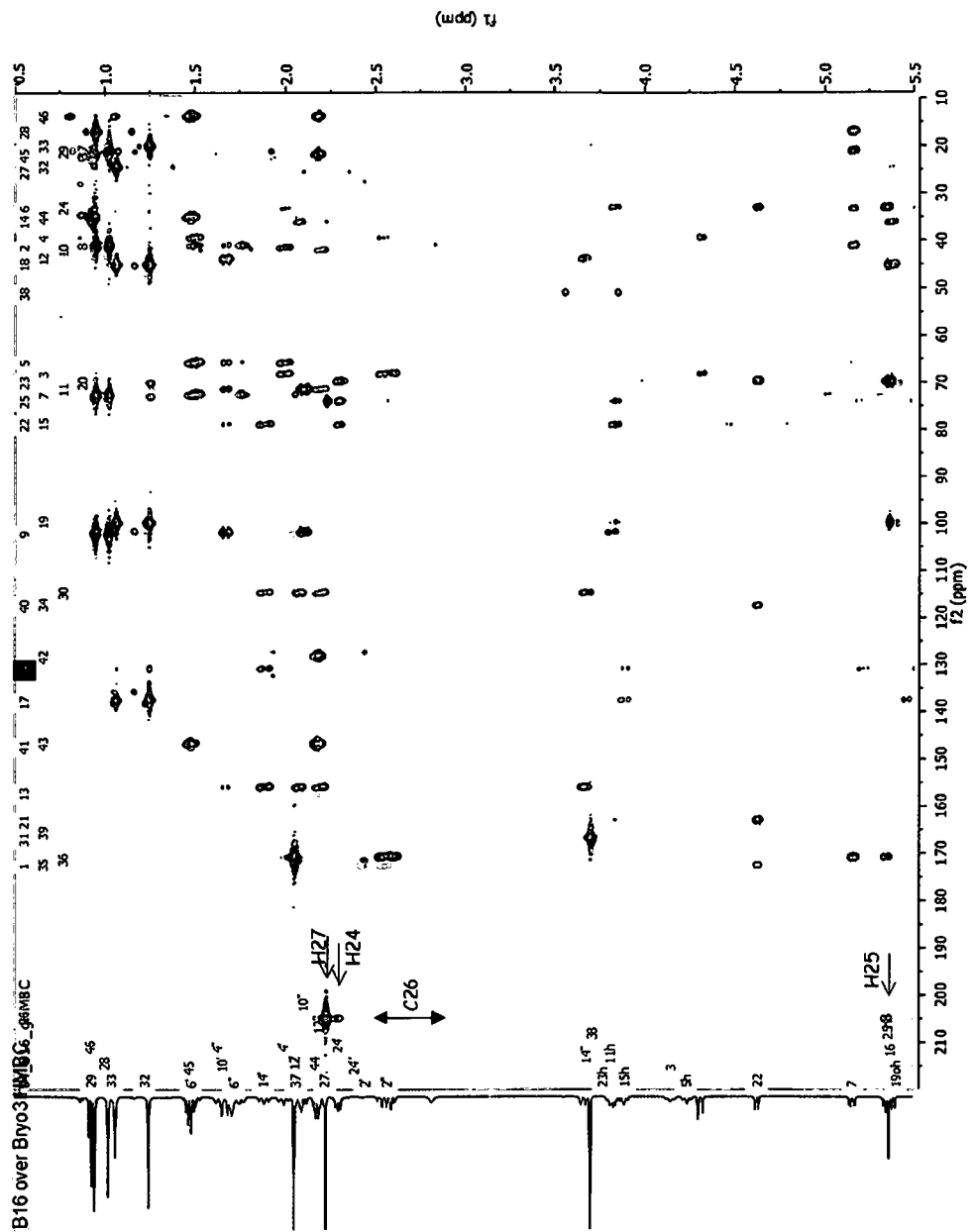

These structures are suggested by the NMR data which is set forth in NMR spectra in FIGS. 16-18. FIG. 16 depicts the NMR spectra of Bryostatin-3. FIG. 17 depicts the NMR spectra of B10. FIG. 18 depicts the NMR spectra of B12 overlaid on the NMR spectra of Bryostatin-3.

Thus, we have disclosed embodiments of the present invention based on our present understanding of the best mode to make and use these compounds. Those skilled in the art will readily understand that such preferred embodiments are subject to alteration and modification and therefore the present invention should not be limited to the precise details, but should encompass the subject matter of the claims that follow and their equivalents.

The invention claimed is:

1. A method of making a first Bryoid composition comprising the steps of isolating a first Bryoid composition from a source of Bryoids and purifying the first Bryoid composition in a range from 50% to a crystal forming purity wherein said first Bryoid composition has a molecular weight of approximately 896-898 Amu (Mass+Sodium) and 873-875 Amu (monoisotopic mass).

2. The method of making the first Bryoid composition of claim 1 wherein said first Bryoid has a measured mass plus sodium of 897.2 Amu and a measured monoisotopic mass of 874.2 Amu.

3. The method of making the first Bryoid composition of claim 1 comprising the steps of:
   (i) extracting the first Bryoid with organic solvents or with SuperFluids (near-critical and supercritical fluids with or without cosolvents) solvents;
   (ii) partially purifying the first Bryoid by silica chromatography with organic solvents or SuperFluids chromatography;
   (iii) performing segmentation chromatography on resulting polymeric resin to improve purity of the first Bryoid;
   (iv) performing C18 chromatography to further improve the purity of the first Bryoid; and
   (v) crystalizing the first Bryoid to still further improve the purity of the first Bryoid.

* * * * *